(12) United States Patent
Menez et al.

(10) Patent No.: US 7,208,616 B2
(45) Date of Patent: Apr. 24, 2007

(54) CIS-DIIODO-(TRANS-L-1,2-CYCLOHEXANEDIAMINE) PLATINUM (II) COMPLEX AND PROCESSES FOR PREPARING HIGH PURITY OXALIPLATIN

(75) Inventors: Guillermo Huerta Menez, Toluca (MX); Domenico Fimognari, Milan (IT)

(73) Assignee: Sicor, Inc., Irvine, CA (US)

( * ) Notice: Subject to any disclaimer, the term of this patent is extended or adjusted under 35 U.S.C. 154(b) by 0 days.

(21) Appl. No.: 11/178,290

(22) Filed: Jul. 12, 2005

(65) Prior Publication Data

US 2006/0041012 A1 Feb. 23, 2006

Related U.S. Application Data

(60) Provisional application No. 60/591,209, filed on Jul. 27, 2004, provisional application No. 60/586,729, filed on Jul. 12, 2004.

(51) Int. Cl.
*C07F 15/00* (2006.01)
*A01N 55/02* (2006.01)
*A61K 31/28* (2006.01)

(52) U.S. Cl. ...................... 556/137; 514/492
(58) Field of Classification Search ........... 556/137; 514/492
See application file for complete search history.

(56) References Cited

U.S. PATENT DOCUMENTS

| | | | |
|---|---|---|---|
| 4,169,846 A | 10/1979 | Kidani et al. | |
| 4,200,583 A | 4/1980 | Kidani et al. | |
| 5,290,961 A | 3/1994 | Okamoto et al. | |
| 5,298,642 A * | 3/1994 | Tozawa et al. | 556/137 |
| 5,338,874 A | 8/1994 | Nakanishi et al. | |
| 6,673,805 B2 * | 1/2004 | Lauria et al. | 514/283 |

FOREIGN PATENT DOCUMENTS

| | | |
|---|---|---|
| EP | 0 376 076 A | 7/1990 |
| EP | 0 617 043 A | 9/1994 |
| EP | 0801070 | 10/1997 |
| EP | 0567438 | 1/1999 |
| EP | 0567438 B1 * | 1/1999 |
| EP | 0625523 | 10/2001 |
| JP | 09132583 | 5/1997 |
| WO | WO 2005/035544 | 4/2005 |
| WO | WO 03/004505 | 1/2006 |

OTHER PUBLICATIONS

Junichi, English abstract of JP 09132583, STN Caplus database, AN 1997:449012.
PCT International Search Report PCT/US2005/024493.

* cited by examiner

*Primary Examiner*—Samuel A Barts
*Assistant Examiner*—Lalitha Nagubandi
(74) *Attorney, Agent, or Firm*—Kenyon & Kenyon LLP

(57) ABSTRACT

The present invention is related to pure cis-diiodo-(trans-L-1,2-cyclohexanediamine) Pt (II) complex, and a process of its preparation. The present invention is further related to the preparation of oxaliplatin using said cis-diiodo-(trans-L-1,2-cyclohexanediamine) Pt (II) complex.

17 Claims, No Drawings

CIS-DIIODO-(TRANS-L-1,2-CYCLOHEXANEDIAMINE) PLATINUM (II) COMPLEX AND PROCESSES FOR PREPARING HIGH PURITY OXALIPLATIN

CROSS-REFERENCE TO RELATED APPLICATIONS

This application claims the benefits of U.S. Provisional Application No. 60/586,729 filed on Jul. 12, 2004 and U.S. Provisional Application No. 60/591,209 filed on Jul. 27, 2004, the disclosures of which are incorporated by reference.

BACKGROUND

Oxaliplatin, cis-oxalato-(trans-L-1,2-cyclohexanediamine)-platinum (II) complex, has the following structure:

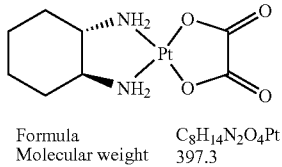

Formula C$_8$H$_{14}$N$_2$O$_4$Pt
Molecular weight 397.3

(1)

Oxaliplatin is slightly soluble in water at 6 mg/mL, very slightly soluble in methanol, and practically insoluble in ethanol and acetone.

Oxaliplatin is marketed as ELOXATIN™ (oxaliplatin for injection), available from Sanofi Aventis US, which is supplied in vials containing 50 mg or 100 mg of oxaliplatin as a sterile, preservative-free lyophilized powder for reconstitution (PDR®; Eloxatin for injection—Complete Monograph).

Oxaliplatin is an antineoplastic agent similar to cisplatin. It is given with fluorouracil and folinic acid in the treatment of metastatic colorectal cancer and in the adjuvant treatment of stage III (Dukes C) colon cancer.

U.S. Pat. No. 4,169,846 claimed oxaliplatin per se and its preparation by a process which yielded it in very low amounts. Improved methods for producing a mixture of trans-D- and trans-L-isomers of oxaliplatin were then disclosed in the patent literature, such as JP 09132583, EP 0625523, EP 0801070, U.S. Pat. No. 5,290,961, U.S. Pat. No. 5,298,642, U.S. Pat. No. 5,338,874 and EP 0567438. These methods involve the preparation of a dihalogen cis-platinum (II) complex of 1,2-diaminocyclohexane of formula (4),

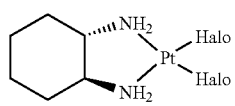

(4)

wherein the dihalogen are Cl, Br or I, which is converted to cis-diaquo-1,2-diaminocyclohexane platinum (II) complex of formula (3),

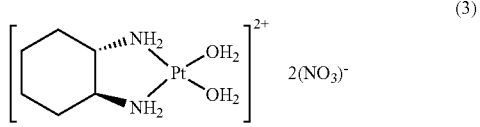

(3)

which is then reacted with oxalic acid or potassium oxalate to obtain the mixture of trans-D- and trans-L-isomers of oxaliplatin.

In EP 0567438, this process is described as a one-pot process, in which the compound of formula (4) is directly converted into the compound of formula (3), without its isolation.

An alternative synthetic route disclosed in EP 0625523 is through the reaction of dihalogen cis-platinum (II) complex of 1,2-diaminocyclohexane of formula (4), wherein the dihalogen are Cl or Br, with silver oxalate, followed by the removal of the silver chloride formed.

EP 0567438 further provides a high purity process to obtain oxaliplatin, where optical resolution of the D-isomer and L-isomer of cis-oxalato-(trans-D,L-1,2-cyclohexanediamine) Pt(II) is conducted by an HPLC method.

Another process for obtaining oxaliplatin is described in WO 2005/035544. This route of synthesis goes through diaquo-(1,2-cyclohexanediamine)Pt(II) of formula (3), in a lengthy process, which requires tedious workup in order to obtain the desired oxaliplatin in high purity.

There still remains a need for processes for the preparation of oxaliplatin, which produce optically pure oxaliplatin in improved and industrial methods.

SUMMARY OF THE INVENTION

One aspect of the present invention relates to isolated cis-diiodo-(trans-L-1,2-cyclohexanediamine) Pt (II) complex of formula (2).

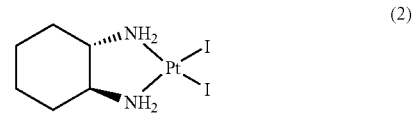

(2)

The cis-diiodo-(trans-L-1,2-cyclohexanediamine) Pt (II) complex of the present invention is characterized by a melting point ranging from about 275° C. to about 300° C. The cis-diiodo-(trans-L-1,2-cyclohexanediamine) Pt (II) complex of the present invention is optically pure, wherein the level of the cis-diiodo-(trans-D-1,2-cyclohexanediamine) Pt (II) complex isomer is less than about 3% area by HPLC, preferably less than about 2% area by HPLC, more preferably less than about 1% area by HPLC, and most preferably less than about 0.1% area by HPLC.

Another aspect of the present invention relates to an optically pure cis-diiodo-(trans-L-1,2-cyclohexanediamine) Pt (II) complex, wherein the level of the cis-diiodo-(trans-D-1,2-cyclohexanediamine) Pt (II) complex isomer is less than about 3% area by HPLC, preferably less than about 2% area by HPLC, more preferably less than about 1% area by HPLC, and most preferably less than about 0.1% area by HPLC.

A further aspect of the present invention relates to a process for preparing cis-diiodo-(trans-L-1,2-cyclohexanediamine) Pt (II) complex, by reacting trans-L-1,2-cyclohexanediamine with potassium tetrachloroplatinate and potassium iodide in water. Preferably, the trans-L-1,2-cyclohexanediamine used is optically pure, wherein the level of the trans-D-1,2-cyclohexanediamine isomer is less than about 3% area by HPLC, preferably less than about 2% area by HPLC, more preferably less than about 1%, and most preferably less than about 0.1% area by HPLC; thus the obtained cis-diiodo-(trans-L-1,2-cyclohexanediamine) Pt (II) complex is also optically pure, as described above.

Yet another aspect the present invention relates to a process for preparing oxaliplatin using the cis-diiodo-(trans-L-1,2-cyclohexanediamine) Pt (II) complex through its reaction with silver oxalate. Preferably, the cis-diiodo-(trans-L-1,2-cyclohexanediamine) Pt (II) complex used is optically pure as described above, thus rendering the oxaliplatin obtained by this process also optically pure.

In another aspect, the present invention relates to a process for preparing oxaliplatin by preparing cis-diiodo-(trans-L-1,2-cyclohexanediamine) Pt (II) complex, preferably optically pure as described above, and converting it to oxaliplatin.

In one aspect, the present invention relates to the process for preparing oxaliplatin comprising the steps of: preparing cis-diiodo-(trans-L-1,2-cyclohexanediamine) Pt (II) complex of formula (2), preferably optically pure,

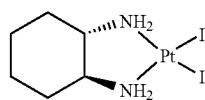

(2)

reacting it with $AgNO_3$ to obtain the cis-diaquo-1,2-diaminocyclohexane platinum (II) complex of formula (3),

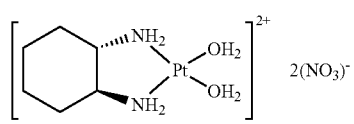

(3)

and reacting the compound of formula (3) with potassium oxalate to obtain oxaliplatin.

In another aspect, the present invention relates to a process for preparing oxaliplatin by preparing the cis-diaquo-1,2-diaminocyclohexane platinum (II) complex from cis-diiodo-(trans-L-1,2-cyclohexanediamine) Pt (II) complex as described above, and converting it to oxaliplatin.

The detailed procedures are described herein below.

DETAILED DESCRIPTION OF THE INVENTION

The term "optical purity" relates to the amount of the desired isomer present in the compound in question.

As used herein, the term "optically pure", in reference to oxaliplatin, cis-diiodo-(trans-L-1,2-cyclohexanediamine) Pt (II) complex and trans-L-1,2-cyclohexanediamine, relates to a level of the unwanted trans isomer of less than about 3% area by HPLC, preferably less than about 2% area by HPLC, more preferably less than about 1%, and most preferably less than about 0.1% area by HPLC. The unwanted isomer of oxaliplatin is cis-oxalato-(trans-D-1,2-cyclohexanediamine) Pt (II) complex. The unwanted isomer of cis-diiodo-(trans-L-1,2-cyclohexanediamine) Pt (II) complex is cis-diiodo-(trans-D-1,2-cyclohexanediamine) Pt (II) complex. The unwanted isomer of trans-L-1,2-cyclohexanediamine is trans-D-1,2-cyclohexanediamine. The optical purity of oxaliplatin is determined with the standard method of the European Pharmacopoeia.

The term "crude" refers to a compound that has not undergone further purification by any known methods, such as, crystallization from or suspension in appropriate solvents.

The present invention provides the isolated cis-diiodo-(trans-L-1,2-cyclohexanediamine) Pt (II) complex of formula (2):

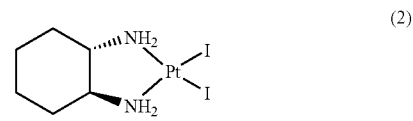

(2)

The cis-diiodo-(trans-L-1,2-cyclohexanediamine) Pt (II) complex of the present invention is characterized by a melting point ranging from about 275° C. to about 300° C. The cis-diiodo-(trans-L-1,2-cyclohexanediamine) Pt (II) complex of the present invention is further characterized by its high optical purity, wherein the level of the cis-diiodo-(trans-D-1,2-cyclohexanediamine) Pt (II) complex isomer is less than about 3% area by HPLC, preferably less than about 2% area by HPLC, more preferably less than about 1% area by HPLC, and most preferably less than about 0.1% area by HPLC.

The cis-diiodo-(trans-L-1,2-cyclohexanediamine) Pt (II) complex of the present invention can be characterized by NMR spectra recorded on a Brucher 300 MHz as follows:

$C^{13}$ NMR, DMSO (ppm): 64.45; 61.13; 32.67; 32.09; 24.91; 24.65;

$H^1$NMR, DMSO (Delta ppm): 2.35, broad singlet, 2H; 1.95, dd, 2H; 1.45, broad singlet, 2H; 1.30, broad singlet, 2H; 1.00, broad singlet, 2H; 6.17 multiplet, ($NH_2$);

Pt 195 NMR, DMSO: −3543 s.

The present invention further provides optically pure cis-diiodo-(trans-L-1,2-cyclohexanediamine) Pt (II) complex, wherein the level of the cis-diiodo-(trans-D-1,2-cyclohexanediamine) Pt (II) complex isomer is less than about 3% area by HPLC, preferably less than about 2% area by HPLC, more preferably less than about 1%, and most preferably less than about 0.1% area by HPLC.

The present invention further provides a process for the preparation of the cis-diiodo-(trans-L-1,2-cyclohexanediamine) Pt (II) complex. This process comprises:

a) combining an aqueous solution of trans-L-1,2-cyclohexanediamine of the formula (5)

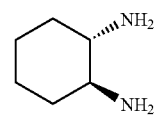

(5)

with an aqueous solution of $M_2PtX_4$ and KI, to obtain a mixture;

b) maintaining the mixture at room temperature; and c) recovering cis-diiodo-(trans-L-1,2-cyclohexanediamine) Pt (II) complex.

wherein M is Li, Na or K, and wherein X is I, Cl or Br.

Preferably, the trans-L-1,2-cyclohexanediamine used in step a) is optically pure. Using such optically pure starting material results in the formation of a product that is also optically pure, without the need for tedious optical resolution methods, such as HPLC. The trans-L-1,2-cyclohexanediamine is commercially available.

Most preferably, M is K. Most preferably, X is I.

The cis-diiodo-(trans-L-1,2-cyclohexanediamine) Pt (II) complex may be recovered by any method known in the art, e.g. a method comprising filtering the reaction solvents and any impurities present, washing the obtained material and drying by any conventional method. In this case, the obtained material can be washed and suspended in water, in order to dispose of halogen ions.

The use of KI has been disclosed in U.S. Pat. No. 5,290,961 and WO 03/004505 to generate iodine compounds, which are removed from the reaction mixture. In the present invention, KI is used to generate the cis-diiodo-(trans-L-1,2-cyclohexanediamine) platinum (II) complex as the key intermediate for the preparation of oxaliplatin.

To further purify the cis-diiodo-(trans-L-1,2-cyclohexanediamine) Pt (II) complex, the product of step c) may be suspended in a solvent selected from the group consisting of an amide, a $C_{1-4}$ alkyl ester, a ketone, a halogenated hydrocarbon, water and a mixture thereof, followed by recovering of the purified material by the methods described above.

The purification process may be repeated in order to obtain an even further purified cis-diiodo-(trans-L-1,2-cyclohexanediamine) Pt (II) complex.

The amide may be methylformamide or dimethylformamide, preferably dimethylformamide. A preferred $C_{1-4}$ alkyl ester is ethyl acetate and methyl acetate. Preferably, the ketone is acetone. The halogenated hydrocarbon is preferably carbon tetrachloride, chloroform or dichloromethane.

Most preferably, the solvent is dimethylformamide.

The invention further provides a process for preparing cis-oxalato-(trans-L-1,2-cyclohexanediamine) Pt (II) complex, i.e. oxaliplatin, involving the cis-diiodo-(trans-L-1,2-cyclohexanediamine) platinum (II) complex and silver oxalate comprising:

(i) providing cis-diiodo-(trans-L-1,2-cyclohexanediamine) platinum (II) complex, preferably optically pure (having less than about 3% area by HPLC of the cis-diiodo-(trans-D-1,2-cyclohexanediamine) platinum (II) complex isomer), for example, by conducting a process for preparing the cis-diiodo-(trans-L-1,2-cyclohexanediamine) platinum (II) complex according to the present invention;

(ii) reacting the cis-diiodo-(trans-L-1,2-cyclohexanediamine) platinum (II) complex with silver oxalate to obtain a reaction mixture;

(iii) mixing the reaction mixture with a potassium salt of the form KX to form oxaliplatin, wherein KX is KCl, KBr or KI; and (iv) recovering the oxaliplatin.

In this process for preparing oxaliplatin involving the cis-diiodo-(trans-L-1,2-cyclohexanediamine) platinum (II) complex and silver oxalate according to the present invention, step (ii) can be performed by:

A) combining the cis-diiodo-(trans-L-1,2-cyclohexanediamine) platinum (II) complex with an aqueous basic solution of silver oxalate to obtain a reaction mixture; and B) heating the reaction mixture to a temperature of about 55° C. to about 75° C. for at least 3 hours;

and steps (iii) and (iv) can be performed by

C) combining the reaction mixture from step B) with the potassium salt of the form KX;

D) maintaining the reaction mixture from step C) for at least 4 hours; and

E) recovering oxaliplatin from the reaction mixture obtained in step D).

One of the embodiments of this process for preparing oxaliplatin involving the cis-diiodo-(trans-L-1,2-cyclohexanediamine) platinum (II) complex and silver oxalate according to the present invention comprises a) combining an aqueous solution of cis-diiodo-(trans-L-1,2-cyclohexanediamine) platinum (II) complex with a basic solution of silver oxalate to obtain a reaction mixture;

b) heating the reaction mixture to a temperature of about 55° C. to about 75° C., preferably about 55° C. to about 60° C., for at least 3 hours;

c) combining the reaction mixture of step b) with a halogenated potassium salt of the form KX;

d) maintaining the reaction mixture for at least 4 hours; and e) recovering oxaliplatin from the reaction mixture, wherein the potassium salt of the form KX is KCl, KBr, or KI.

In the process for preparing oxaliplatin involving the cis-diiodo-(trans-L-1,2-cyclohexanediamine) platinum (II) complex and silver oxalate, the basic solution of silver oxalate preferably has a pH of about 4.5 to about 5.0. Preferably, the basic solution of silver oxalate is obtained by dissolving silver oxalate in a solution of an alkali hydroxide base, preferably NaOH or KOH. Preferably, the potassium salt of the form KX is KI.

Oxaliplatin may be recovered from a preparative process involving cis-diiodo-(trans-L-1,2-cyclohexanediamine) platinum (II) complex of the present invention. Preferably, the reaction mixture is filtered in order to remove any impurities such as precipitated silver halide compound, obtained by a reaction of the silver ions with the halogen ions present in the reaction mixture. The obtained filtrate can be cooled to a temperature of about 0° C. to about 5° C. at which crude oxaliplatin is formed. The crude oxaliplatin may be filtered, washed and dried, by any methods known in the art.

Preferably, the cis-diiodo-(trans-L-1,2-cyclohexanediamine) platinum (II) complex used in a process for preparing oxaliplatin involving the cis-diiodo-(trans-L-1,2-cyclohexanediamine) platinum (II) complex and silver oxalate according to the present invention has less than about 3% area by HPLC, preferably less than 2% area by HPLC, more preferably less than 1% area by HPLC, and most preferably less than 0.1% area by HPLC, of the unwanted isomer, and thus the obtained oxaliplatin also contains low levels, e.g. less than 3% area by HPLC, preferably less than 2% area by HPLC, more preferably less than 1% area by HPLC and most preferably less than 0.1% area by HPLC, of its respective unwanted isomer.

The crude oxaliplatin obtained is preferably crystallized by dissolving it in water at a temperature of about 55° C. to about 70° C., and cooling the obtained solution to a temperature of about 0° C. to about 5° C. The crystallization in water may be repeated a number of times, combined with the removal of the remaining silver ions from the reaction mixture. The silver ions may be eliminated preferably by addition of a potassium halogenated salt such as KI, KCl or KBr, preferably KI, to the solution of oxaliplatin in water, so that the excess Ag+ reacts with the halogen ions to form a precipitate of silver halide. The formed silver halide compound may be removed from the solution by filtration using any conventional methods, such as a membrane.

Another way to eliminate the silver ions is by using a chelating agent such as EDTA. Yet another way to dispose of the silver ions is by using a cation exchange resin.

The obtained oxaliplatin may be further recrystallized from a solvent selected from the group consisting of an amide, a $C_{1-4}$ alkyl ester, a ketone, a halogenated hydrocarbon, water and a mixture thereof, followed by recovering of the purified material by the methods described above.

The amide may be methylformamide or dimethylformamide, preferably dimethylformamide. A preferred $C_{1-4}$ alkyl ester is ethyl acetate and methyl acetate. Preferably, the ketone is acetone. The halogenated hydrocarbon is preferably carbon tetrachloride, chloroform or dichloromethane.

Most preferably, the solvent is dimethylformamide.

The oxaliplatin recovered after the re-crystallization processes described above is optically pure, wherein the level of the cis-oxalato-(trans-D-1,2-cyclohexanediamine) Pt (II) complex isomer is less than about 3% area by HPLC. Preferably, the level of the cis-oxalato-(trans-D-1,2-cyclohexanediamine) Pt (II) complex isomer is less than about 2% area by HPLC, more preferably less than about 1% area by HPLC, and most preferably less than about 0.1% area by HPLC.

The use of cis-diiodo-(trans-L-1,2-cyclohexanediamine) platinum (II) complex as an intermediate for preparing oxaliplatin avoids an additional step for obtaining cis-diaquo-1,2-diaminocyclohexane platinum (II) complex of formula (3).

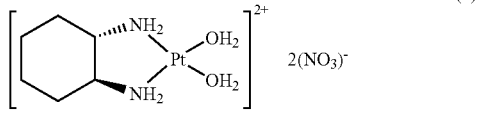

(3)

The present invention also provides a process for preparing oxaliplatin involving cis-diiodo-(trans-L-1,2-cyclohexanediamine) Pt (II) complex comprising:
  a) combining an aqueous solution of trans-L-1,2-cyclohexanediamine of the formula (5)

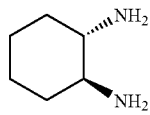

(5)

with an aqueous solution of $M_2PtX_4$ and KI to obtain a mixture;
  b) maintaining the mixture at room temperature;
  c) recovering cis-diiodo-(trans-L-1,2-cyclohexanediamine) Pt (II) complex;
  d) combining the cis-diiodo-(trans-L-1,2-cyclohexanediamine) platinum (II) complex with water, and combining the obtained solution with a basic solution of silver oxalate to obtain a reaction mixture;
  e) heating the reaction mixture to a temperature of about 55° C. to about 75° C. for at least 3 hours;
  f) combining the reaction mixture of step e) with a halogenated potassium salt of the form KX;
  g) maintaining the reaction mixture for at least 4 hours; and
  h) recovering oxaliplatin from the reaction mixture,
  wherein M is Li, Na or K,
  wherein X is I, Cl or Br, and
  wherein the potassium salt of the form KX is KCl, KBr, or KI.

Preferably, the trans-L-1,2-cyclohexanediamine used in step a) is optically pure, which results in an optically pure oxaliplatin.

Cis-diiodo-(trans-L-1,2-cyclohexanediamine) platinum (II) complex may be also converted into oxaliplatin via the cis-diaquo-1,2-diaminocyclohexane platinum (II) complex of formula (3).

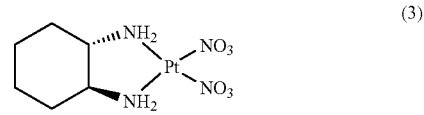

(3)

The present invention provides a process for preparing oxaliplatin involving cis-diiodo-(trans-L-1,2-cyclohexanediamine) platinum (II) complex and cis-diaquo-(trans-L-1,2-cyclohexanediamine) Pt (II) complex, comprising:
  (i) providing cis-diiodo-(trans-L-1,2-cyclohexanediamine) platinum (II) complex, preferably optically pure (having less than about 3% area by HPLC of the cis-diiodo-(trans-D-1,2-cyclohexanediamine) platinum (II) complex isomer), for example, by conducting a process for preparing the cis-diiodo-(trans-L-1,2-cyclohexanediamine) platinum (II) complex according to the present invention;
  (ii) reacting the cis-diiodo-(trans-L-1,2-cyclohexanediamine) platinum (II) complex with silver nitrate to obtain cis-diaquo-(trans-L-1,2-cyclohexanediamine) Pt (II) complex in a reaction mixture;
  (iii) removing silver ions from the reaction mixture;
  (iv) recovering the cis-diaquo-(trans-L-1,2-cyclohexanediamine) Pt (II) complex;
  (v) converting the cis-diaquo-(trans-L-1,2-cyclohexanediamine) Pt (II) complex to oxaliplatin; and
  (vi) recovering the oxaliplatin.

In the process for preparing oxaliplatin involving cis-diiodo-(trans-L-1,2-cyclohexanediamine) platinum (II) complex and cis-diaquo-(trans-L-1,2-cyclohexanediamine) Pt (II) complex according to the present invention, step (ii) can be performed by
  I) combining the cis-diiodo-(trans-L-1,2-cyclohexanediamine) platinum (II) complex with an aqueous solution of silver nitrate to obtain a reaction mixture;
  II) heating the reaction mixture to a temperature of about 45° C. to about 60° C., preferably about 45° C. to about 55° C., to obtain a suspension of cis-diaquo-(trans-L-1,2-cyclohexanediamine) Pt (II) complex; and optionally further comprising
  III) cooling the suspension to a temperature of about 20° C. to about 30° C.

In the process for preparing oxaliplatin involving cis-diiodo-(trans-L-1,2-cyclohexanediamine) platinum (II) complex and cis-diaquo-(trans-L-1,2-cyclohexanediamine) Pt (II) complex according to the present invention, the silver ions can be removed from the reaction mixture by the precipitation of silver iodide obtained from the addition of KI.

In the process for preparing oxaliplatin involving cis-diiodo-(trans-L-1,2-cyclohexanediamine) platinum (II) complex and cis-diaquo-(trans-L-1,2-cyclohexanediamine) Pt (II) complex according to the present invention, the cis-diaquo-(trans-L-1,2-cyclohaxanediamine) Pt (II) complex can be converted into oxaliplatin by combining it with potassium oxalate; adjusting the pH to about 4.5 to about 5.0; cooling to obtain a suspension of cis-oxalato-(trans-L-1,2-cyclohexanediamine) Pt (II) complex; and recovering cis-oxalato-(trans-L-1,2-cyclohexanediamine) Pt (II) complex from the suspension.

One of the embodiments of the process for preparing oxaliplatin involving cis-diiodo-(trans-L-1,2-cyclohexanediamine) platinum (II) complex and cis-diaquo-(trans-L-1,2-cyclohexanediamine) Pt (II) complex according to the present invention comprises:

a) combining an aqueous solution of cis-diiodo-(trans-L-1,2-cyclohexanediamine) Pt (II) complex with an aqueous solution of silver nitrate to obtain a reaction mixture;

b) heating the reaction mixture to a temperature of about 45° C. to about 60° C. to obtain a suspension of cis-diaquo-(trans-L-1,2-cyclobaxanediamine) Pt (II) complex;

c) cooling the suspension to a temperature of about 20° C. to about 30° C.;

d) removing the silver ions from the reaction mixture;

e) recovering cis-diaquo-(trans-L-1,2-cyclohaxanediamine) Pt (II) complex; and f) converting the cis-diaquo-(trans-L-1,2-cyclohaxanediamine) Pt (II) complex to oxaliplatin.

Preferably, the reaction mixture in step b) is heated to a temperature of about 45° C. to about 55° C. Preferably, the silver ions are removed from the reaction mixture by the addition of KI so that silver iodide precipitates, and is eliminated from the reaction mixture, for example, by filtration.

Preferably, the cis-diiodo-(trans-L-1,2-cyclohexanediamine) Pt (II) complex used in step a) is optically pure, thus rendering the obtained cis-diaquo-(trans-L-1,2-cyclohaxanediamine) Pt (II) complex also optically pure.

The cis-diaquo-(trans-L-1,2-cyclohaxanediamine) Pt (II) complex may be converted to oxaliplatin according to the methods known in the art, such as the process described in U.S. Pat. No. 5,338,874.

In a preferred embodiment, the cis-diaquo-(trans-L-1,2-cyclohaxanediamine) Pt (II) complex is converted into oxaliplatin by combining it with potassium oxalate; adjusting the pH to about 4.5 to about 5.0 with an aqueous solution of an alkali hydroxide base; cooling to obtain a suspension of cis-oxalato-(trans-L-1,2-cyclohexanediamine) Pt (II) complex, and recovering cis-oxalato-(trans-L-1,2-cyclohexanediamine) Pt (II) complex from the suspension.

Potassium oxalate may preferably be prepared from oxalic acid and potassium hydroxide.

The complete synthetic route of one of the embodiments of the present invention is presented below:

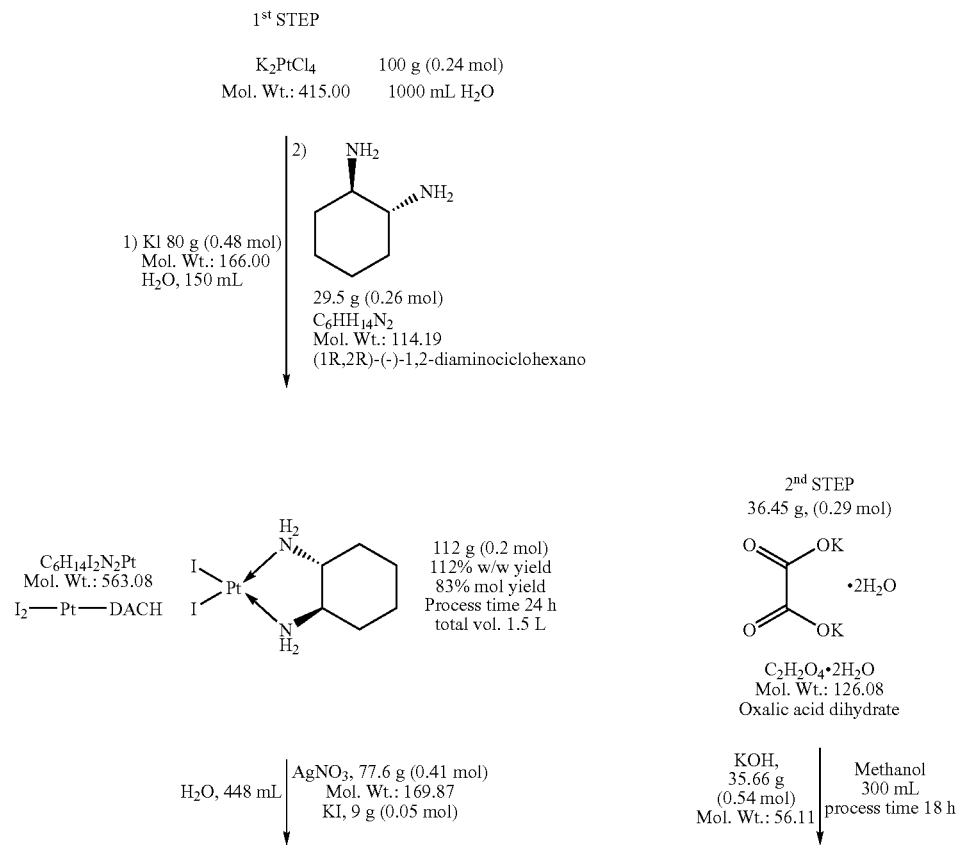

-continued

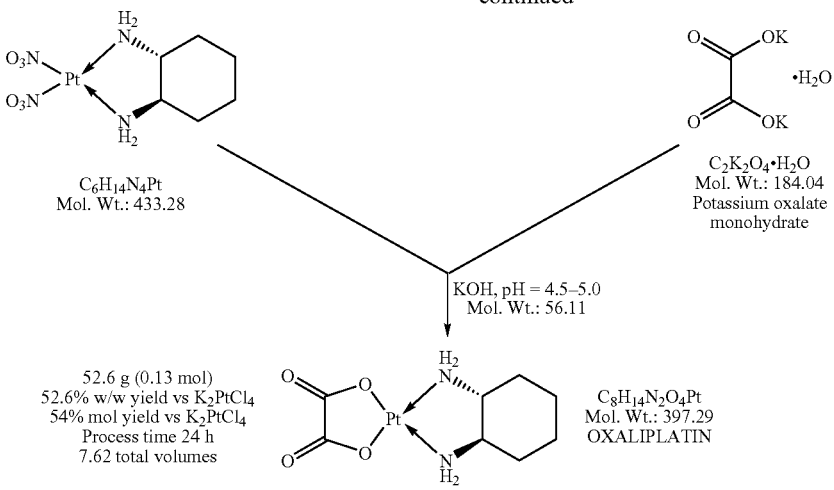

The lower solubility of AgI compared to AgCl and AgBr permits the formation of a cis-diaquo-(trans-L-1,2-cyclohexanediamine) Pt (II) complex of very good quality. Moreover, the reaction of the cis-dihalo-(trans-1,2-diaminocyclohexane)platinum (II) complex, wherein halo is Br or Cl, with $AgNO_3$ in the methods described in the prior art requires a reaction time between 24 and 72 hours. In the method of the present invention, however, the cis-diiodo-(trans-L-1,2-cyclohexanediamine) Pt (II) complex is converted into the cis-diaquo-(trans-L-1,2-cyclohexanediamine) Pt (II) complex in less than two hours.

The present invention also provides a process for the preparation of the oxaliplatin, comprising:

a) combining an aqueous solution of trans-L-1,2-cyclohexanediamine of the formula (5)

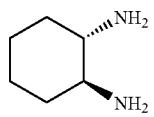 (5)

with an aqueous solution of $M_2PtX_4$ and KI, to obtain a mixture;

b) maintaining the mixture at room temperature;

c) recovering cis-diiodo-(trans-L-1,2-cyclohexanediamine) Pt (II) complex; and d) converting the cis-diiodo-(trans-L-1,2-cyclohexanediamine) Pt (II) complex into oxaliplatin, wherein M is Li, Na or K, and wherein X is I, Cl or Br.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

EXAMPLES

Example 1

Preparation of cis-diiodo-(trans-L-1,2-cyclohexanediamine) Pt (II) Complex

This process was carried out under nitrogen atmosphere.

34.4 gr. of potassium tetrachloroplatinate were dissolved in 275 ml of water. A solution of 80.1 gr. of KI in 140 ml of water was prepared. Both solutions were mixed for 15 min to obtain a mixed solution, which was then added to an aqueous solution previously prepared with 10 gr. of trans-L-1,2-cyclohexanediamine having an optical purity of at least 99.9% area by HPLC in 30 ml of water. The reaction solution was stirred at room temperature for 10 hours to form crude cis-diiodo-(trans-L-1,2-cyclohexanediamine) Pt (II) complex, which was filtered off from the reaction solution as a precipitate and washed 3 times with 55 ml of water. The precipitate was then re-suspended in 220 ml of water for 15 min and filtered off from the suspension, and washed with water until halogen ions were not detected. The washed precipitate was suspended in 45 ml of dimethylformamide for 15 min. The suspended precipitate was filtered off from the suspension, washed 3 times with 10 ml of dimethylformamide, then washed 3 times with 30 ml of water and finally washed 3 times with 20 ml of acetone to obtain cis-diiodo-(trans-L-1,2-cyclohexanediamine) Pt (II) complex, which was dried under vacuum at 25°–30° C. for 12 hours to obtain pure cis-diiodo-(trans-L-1,2-cyclohexanediamine) Pt (II) complex having a m.p. between 275°–300° C., an optical purity of at least 99.5% area by HPLC, and a weight of 40.0 gr.

Example 2

Preparation of cis-diiodo-(trans-L-1,2-cyclohexanediamine) Pt (II) Complex 100 g of potassium tetrachloroplatinate were dissolved in 1000 mL of water at 15–25° C. and stirred for 20 min., then the solution was filtered through a buchner funnel with filter paper. In a separate flask, 80.0 g of KI and 150 mL of water were charged at room temperature; then the solutions of KI and $K_2PtCl_4$ were mixed and stirred for 20 min at 20–30° C. To the solution obtained, a mixture of trans-L-1,2-cyclohexanediamine (DACH) (29.5 g) and water (70 mL) was slowly added. The reaction mixture was stirred at 20–30° C. for 3 hrs. The solid product was filtered off under vacuum on buchner funnel and washed with water (3×300 mL). The product was dried in a vacuum oven at 65° C. at least for 12 hrs. The cis-diiodo-(trans-L-1,2-cyclohexanediamine) Pt (II) complex product had an optical purity of at least 99.5% area by HPLC.

Example 3

Preparation of cis-diiodo-(trans-L-1,2-cyclohexanediamine) Pt (II) Complex

This process was carried out under nitrogen atmosphere.

34.4 gr. of potassium tetrachloroplatinate were dissolved in 275 ml of water. A solution of 80.1 gr. of KI in 140 ml of water was prepared. Both solutions were mixed for 15 min to obtain a mixed solution, which was then added to an aqueous solution previously prepared with 10 gr. of trans-L-1,2-cyclohexanediamine having an optical purity of at least 99.9% area by HPLC in 30 ml of water. The reaction solution was stirred at room temperature for 10 hrs to form crude cis-diiodo-(trans-L-1,2 cyclohexanediamine) Pt (II) complex, which was filtered off from the reaction solution as a precipitate and washed 3 times with 55 ml of water. The precipitate was then re-suspended in 220 ml of water for 15 min and filtered off from the suspension, and washed with water until halogen ions were not detected. The washed precipitate was suspended in 45 ml of a solution previously prepared with 50% of dimethylformamide and 50% of water for 15 min. The suspended precipitate was filtered off from the suspension, washed 3 times with 10 ml of the solution 50% dimethylformamide/water, then washed 3 times with 30 ml of water and finally washed 3 times with 20 ml of acetone to obtain cis-diiodo-(trans-L-1,2 cyclohexanediamine) Pt (II) complex, which was dried under vacuum at 25°–30° C. for 12 hrs to obtain pure cis-diiodo-(trans-L-1,2 cyclohexanediamine) Pt (II) complex. The pure cis-diiodo-(trans-L-1,2 cyclohexanediamine) Pt (II) complex (2) obtained had a m.p. between 275°300° C., an optical purity of at least 99.5% area by HPLC, and a weight of 37.0 gr.

Example 4

Preparation of cis-diaquo-(trans-L-1,2-cyclohexanediamine) Pt (II) Complex 100 g of platinum cis-diiodo-(trans-L-1,2-cyclohexanediamine) Pt (II) complex and 400 mL of water were charged at 20–30° C. and stirred for 20 min. To the previous solution a mixture prepared with $AgNO_3$ (69.3 g) and water (100–130 mL) was added. The mixture was stirred for 60 min at 20–30° C., then heated to 45–55° C. and stirred for 10 min. The suspension was then cooled at 20–30° C. and 8 g of KI in 20 ml of water were added and the suspension was stirred for 20 minutes. The obtained silver iodide was filtered off under vacuum and washed with water (2×100 mL). The obtained solution was kept under darkness ready to use in the next step.

Example 5

Preparation of Potassium Oxalate

Under stirring, 35.66 g of potassium hydroxide were dissolved in 300 mL of MeOH and 36.45 g of oxalic acid was charged into the solution at room temperature. The mixture was stirred for 3 hours. The solvent was distilled off at atmospheric pressure until 100 mL of total volume. The salt was filtered off under vacuum, washed with MeOH (3×20 mL) and dried under vacuum at room temperature at least for 12 h.

Example 6

Preparation of Cis-oxalato-(trans-L-1 2-cyclohexanediamine) Pt (II) Complex

The process for preparing the cis-oxalato-(trans-L-1,2-cyclohexanediamine) Pt (II) complex (1) was performed under nitrogen atmosphere and in dim light because the cis-oxalato-(trans-L-1,2-cyclohexanediamine) Pt (II) complex (1) is light sensitive. 10 gr. of cis-diiodo-(trans-L-1,2-cyclohexanediamine) Pt (II) complex (2) were dissolved in 800 ml of water. Then 5.4 gr of silver oxalate was added to the solution and the pH was adjusted to 4.5–5.0 with 0.1N NaOH solution. The reaction solution was heated at 55–60° C. for 3 hrs, and 0.05 gr. of KI was added and stirred at the same temperature for 4 hrs. Then 0.1 gr. of charcoal was added and was filtered off at 55°–60° C. together with AgI with a 0.2 µm membrane. The filtrate was concentrated under vacuum at 55–60° C. to a volume of 70 ml and cooled at 0–5° C. over 30 min to form crude cis-oxalato-(trans-L-1,2-cyclohexanediamine) Pt (II) complex structure (1). The crude cis-oxalato-(trans-L-1,2-cyclohexanediamine) Pt (II) complex structure (1) was filtered off from the solution and washed two times with 10 ml of cooled water. The washed cis-oxalato-(trans-L-1,2-cyclohexanediamine) Pt (II) complex structure (1) was then dried under vacuum at 25°–30° C. for 12 hrs. yielding 5.6 gr. of a crude product (1). The crude cis-oxalato-(trans-L-1,2-cyclohexanediamine) Pt (II) complex product (1) was crystallized via dissolution in 450 ml of water at 55–60° C., the addition of 0.05 gr. of charcoal at this temperature and filtration through a 0.2 µm membrane; and then the filtrate was concentrated under vacuum at 55–60° C. to a volume of 40 ml and cooled at 0°–5° C. for 30 min to form a precipitate. The precipitate was filtered off and washed 3 times with 5.0 ml of water. The cis-oxalato-(trans-L-1,2-cyclohexanediamine) Pt (II) complex product (1) was dried under vacuum at 45°–50° C. over 24 hours. The cis-oxalato-(trans-L-1,2-cyclohexanediamine) Pt (II) complex product (1) was purified via re-dissolution of the cis-oxalato-(trans-L-1,2-cyclohexanediamine) Pt (II) complex product (1) in 450 ml of water at 55–60° C., and addition of 0.05 gr. of KI at the same temperature with stirring for 4 hours to eliminate any trace of silver ions. After 0.05 gr. of charcoal were added and filtered off through a 0.2 µm membrane, the filtrate was concentrated under vacuum at 55°–60° C. to a final volume of 40 ml, and cooled at 0°–5° C. for 30 min to form a precipitate. The precipitate was filtered off and washed 3 times with 5.0 ml of water. The cis-oxalato-(trans-L-1,2-cyclohexanediamine) Pt (II) complex product (1) was dried under vacuum at 25°–30° C. over 12 hours. The dried cis-oxalato-(trans-L-1,2-cyclohexanediamine) Pt (II) complex product (1) was suspended in 30 ml of dimethylformamide, stirred for 15 min, filtered off from the suspension and washed 3 times with 5.0 ml of dimethylformamide. Finally, the cis-oxalato-(trans-L-1,2-cyclohexanediamine) Pt (II) complex product (1) was re-suspended in 20 ml of water at room temperature for 15 min, filtered off from the suspension and washed 3 times with 5.0 ml of cooled water to eliminate dimethylformamide. The cis-oxalato-(trans-L-1,2-cyclohexanediamine) Pt (II) complex product (1) was dried under vacuum at 45°–50° C. for 20 hrs. Pure crystals of cis-oxalato-(trans-L-1,2-cyclohexanediamine) Pt (II) complex (1) were obtained with a weight of 5.0 gr. and optical purity of at least 99.9% area by HPLC.

Example 7

Preparation of cis-oxalato-(trans-L-1,2-cyclohexanediamine) Pt (II) Complex

The process for preparing the cis-oxalato-(trans-L-1,2-cyclohexanediamine) Pt (II) complex (1) was performed under nitrogen atmosphere and with dim light because the cis-oxalato-(trans-L-1,2-cyclohexanediamine) Pt (II) complex (1) is light sensitive. 10 gr. of cis-diiodo-(trans-L-1,2-cyclohexanediamine) Pt (II) complex (2) were dissolved in 800 ml of water. Then 5.4 gr. of silver oxalate was added to the solution and the pH was adjusted to 4.5–5.0 with 0.1N NaOH solution (only if needed). The reaction mixture was heated at 55–60° C. for 3 hrs and added 0.05 gr. of KI and stirred at the same temperature for 4 hrs. Then 0.1 gr. of charcoal was added and was filtered off at 55°–60° C. together with AgI with a 0.2 μm membrane. The filtrate was concentrated under vacuum at 55–60° C. to a volume of 70 ml and cooled at 0–5° C. over 30 min to form crude cis-oxalato-(trans-L-1,2-cyclohexanediamine) Pt (II) complex (1). The crude cis-oxalato-(trans-L-1,2-cyclohexanediamine) Pt (II) complex (1) was filtered off from the solution and washed two times with 10 ml of cooled water. The washed cis-oxalato-(trans-L-1,2-cyclohexanediamine) Pt (II) complex (1) was then dried under vacuum at 25°–30° C. for 12 hrs. yielding 5.6 gr. of a crude cis-oxalato-(trans-L-1,2-cyclohexanediamine) Pt (II) complex product (1). The crude cis-oxalato-(trans-L-1,2-cyclohexanediamine) Pt (II) complex product (1) was crystallized via dissolution in 450 ml of water at 55–60° C., the addition of 0.05 gr. of charcoal at this temperature and filtration through a 0.2 μm membrane; and then the filtrate was concentrated under vacuum at 55–60° C. to a volume of 40 ml and cooled at 0°–5° C. for 30 min to form a precipitate. The precipitate was filtered off and washed 3 times with 5.0 ml of water. The cis-oxalato-(trans-L-1,2-cyclohexanediamine) Pt (II) complex product (1) was dried under vacuum at 45°–50° C. oven 24 hrs. The cis-oxalato-(trans-L-1,2-cyclohexanediamine) Pt (II) complex product (1) was purified via re-dissolution of the cis-oxalato-(trans-L-1,2-cyclohexanediamine) Pt (II) complex product (1) in 450 ml of water at 55–60° C., and addition of 0.05 gr of KI at the same temperature with stirring for 4 hours to eliminate any trace of silver ions. After 0.05 gr of charcoal were added and filtered off through a 0.2 μm membrane, the filtrate was concentrated under vacuum at 55°–60° C. to a final volume of 40 ml, and cooled at 0°-5° C. for 30 min to form a precipitate. The precipitate was filtered off and washed 3 times with 5.0 ml of water. The cis-oxalato-(trans-L-1,2-cyclohexanediamine) Pt (II) complex product (1) was dried under vacuum at 25°–30° C. over 12 hrs. The dried cis-oxalato-(trans-L-1,2-cyclohexanediamine) Pt (II) complex product (1) was suspended in 30 ml of a solution of 50% dimethylformamide and 50% water, stirred for 15 min, filtered off from the suspension and washed 3 times with 5.0 ml of the 50% dimethylformamide/water solution. Finally, the cis-oxalato-(trans-L-1,2-cyclohexanediamine) Pt (II) complex product (1) was re-suspended in 20 ml of water at room temperature for 15 min, filtered off from the suspension and washed 3 times with 5.0 ml of cooled water to eliminate dimethylformamide. The cis-oxalato-(trans-L-1,2-cyclohexanediamine) Pt (II) complex product (1) was dried under vacuum at 45°–50° C. for 20 hrs. Pure crystals of cis-oxalato-(trans-L-1,2-cyclohexanediamine) Pt (II) complex (1) were obtained with a weight of 5.4 gr. and optical purity of at least 99.9% area by HPLC.

Example 8

Preparation of cis-oxalato-(trans-L-1,2-cyclohexanediamine) Pt (II) Complex

The process for preparing the cis-oxalato-(trans-L-1,2-cyclohexanediamine) Pt (II) complex (1) should be performed under nitrogen atmosphere and with dim light because the cis-oxalato-(trans-L-1,2-cyclohexanediamine) Pt (II) complex (1) is light sensitive. 10 gr. of cis-diiodo-(trans-L-1,2-cyclohexanediamine) Pt (II) complex (2) were dissolved in 800 ml of water. Then 5.4 gr of silver oxalate was added to the solution and the pH was adjusted to 4.5–5.0 with 0.1N NaOH solution (only if needed). The reaction solution was heated at 70–75° C. for 3 hrs and added 0.05 gr. of KI and stirred at the same temperature for 4 hrs. Then 0.1 gr. of charcoal was added and was filtered off at 70°–75° C. together with AgI with a 0.2 μm membrane. The filtrate was concentrated under vacuum at 70–75° C. to a volume of 70 ml and cooled at 0–5° C. over 30 min to form crude cis-oxalato-(trans-L-1,2-cyclohexanediamine) Pt (II) complex (1). The crude cis-oxalato-(trans-L-1,2-cyclohexanediamine) Pt (II) complex (1) was filtered off from the solution and washed two times with 10 ml of cooled water. The washed cis-oxalato-(trans-L-1,2-cyclohexanediamine) Pt (II) complex (1) was then dried under vacuum at 25°–30° C. for 12 hrs. yielding 5.6 gr. of a crude cis-oxalato-(trans-L-1,2-cyclohexanediamine) Pt (II) complex product (1). The crude cis-oxalato-(trans-L-1,2-cyclohexanediamine) Pt (II) complex product (1) was crystallized via dissolution in 450 ml of water at 70–75° C., the addition of 0.05 gr. of charcoal at this temperature and filtration through a 0.2 μm membrane; and then the filtrate was concentrated under vacuum at 70–75° C. to a volume of 40 ml and cooled at 0°5° C. for 30 min to form a precipitate. The precipitate was filtered off and washed 3 times with 5.0 ml of water. The cis-oxalato-(trans-L-1,2-cyclohexanediamine) Pt (II) complex product (1) was dried under vacuum at 45°–50° C. oven 24 hrs. The cis-oxalato-(trans-L-1,2-cyclohexanediamine) Pt (II) complex product (1) was purified via re-dissolution of the cis-oxalato-(trans-L-1,2-cyclohexanediamine) Pt (II) complex product (1) in 450 ml of water at 70–75° C., and addition of 0.05 gr of KI at the same temperature with stirring for 4 hours to eliminate any trace of silver ions. After 0.05 gr of charcoal were added and filtered off through a 0.2 μm membrane, the filtrate was concentrated under vacuum at 70°–75° C. to a final volume of 40 ml, and cooled at 0°–5° C. for 30 min to form a precipitate. The precipitate was filtered off and washed 3 times with 5.0 ml of water. The cis-oxalato-(trans-L-1,2-cyclohexanediamine) Pt (II) complex product (1) was dried under vacuum at 25°–30° C. over 12 hrs. The dried cis-oxalato-(trans-L-1,2-cyclohexanediamine) Pt (II) complex product (1) was suspended in 30 ml of dimethylformamide, stirred for 15 min, filtered off from the suspension and washed 3 times with 5.0 ml of dimethylformamide. Finally, the cis-oxalato-(trans-L-1,2-cyclohexanediamine) Pt (II) complex product (1) was re-suspended in 20 ml of water at room temperature for 15 min, filtered off from the suspension and washed 3 times with 5.0 ml of cooled water to eliminate dimethylformamide. The cis-oxalato-(trans-L-1,2-cyclohexanediamine) Pt (II) complex product (1) was dried under vacuum at 45°–50° C. for 20 hrs. Pure crystals of cis-oxalato-(trans-L-1,2-cyclohexanediamine) Pt (II) complex (1) were obtained with a weight of 5.0 gr. and optical purity of at least 99.9% area by HPLC.

Example 9

Preparation of cis-oxalato-(trans-L-1,2-cyclohexanediamine) Pt (II) Complex

To the solution of cis-diaquo-(trans-L-1,2-cyclohexanediamine) Pt (II) complex, approximately 54 g potassium oxalate was added and the pH was adjusted to 4.5–5.0 with KOH 0.1 M. The mixture was stirred at least for 2.5 hours. The reaction mixture was cooled down between 5–10° C., and the obtained suspension was filtered off and the solid was washed with 100 mL of a cold mixture prepared with ethanol-water (9:1 v/v). The wet product was then suspended in water (7.0 L) and warmed up until complete solution. The hot solution was filtered under vacuum through a 0.2 mm membrane, in order to eliminate the insoluble impurities, and washed two times with hot water (100 mL). The water was removed under vacuum at 60° C. until 2 L final volume and the precipitate formed was filtered off under vacuum and washed with 100 mL of a cold mixture prepared with ethanol-water (9:1 v/v), then absolute ethanol (100 mL) at 5° C., two washings with 50 ml of DMF at 5° C. and three washings with 50 ml of ethanol. The precipitate was then dried on the funnel with vacuum for 60 min. The product was dissolved with 4.8 L of water at room temperature, filtered through 0.2 mm filter and the solution was concentrated to about 100 mL; the solution was then cooled to 0–5° C. in 30 minutes. The suspension was filtered off and washed twice with 50 ml of a mixture ethanol:water 9:1 vol:vol at 5° C., three times with 30 ml of DMF and twice with 50 ml of ethanol a 0–5° C. The solid was dried under vacuum for 12 hours.

Example 10

Characterization of cis-diiodo-(trans-L-1,2-cyclohexanediamine) Pt (II) Complex

The cis-diiodo-(trans-L-1,2-cyclohexanediamine) Pt (II) complex of the present invention was characterized by NMR spectra recorded on a Brucher 300 MHz as follows:

$C^{13}$ NMR, DMSO (ppm): 64.45; 61.13; 32.67; 32.09; 24.91; 24.65

$H^1$ NMR, DMSO (Delta ppm): 2.35, broad singlet, 2H; 1.95, dd, 2H; 1.45, broad singlet, 2H; 1.30, broad singlet, 2H; 1.00, broad singlet, 2H; 6.17 multiplet, ($NH_2$)

Pt 195 NMR, DMSO: −3543 s.

No significant peaks that could be ascribed to impurities were seen in the NMR spectra.

What is claimed is:

1. A process for preparing oxaliplatin, comprising
(i) conducting a process of preparing cis-diiodo-(trans-L-1,2-cyclohexanediamine) Pt (II) complex comprising:
a) combining trans-L-1,2-cyclohexanediamine of formula (5)

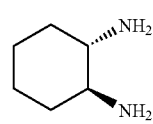

with $M_2PtX_4$ and KI to obtain a mixture;
b) maintaining the mixture at room temperature; and
c) recovering cis-diiodo-(trans-L-1,2-cyclohexanediamine) Pt (II) complex,
wherein M is Li, Na or K, and
wherein X is I, Cl or Br;
(ii) reacting the cis-diiodo-(trans-L-1,2-cyclohexanediamine) platinum (II) complex obtained in step c) with silver oxalate to obtain a reaction mixture;
(iii) mixing the reaction mixture with KY to form oxaliplatin, wherein KY is KCl, KBr or KI; and
(iv) recovering the oxaliplatin.

2. The process of claim 1,
wherein step (ii) is performed by
d) combining the cis-diiodo-(trans-L-1,2-cyclohexanediamine) platinum (II) complex obtained in step c) with an aqueous basic solution of silver oxalate to obtain a reaction mixture; and
e) heating the reaction mixture to a temperature of about 55° C. to about 75° C. for at least 3 hours;
wherein steps (iii) and (iv) are performed by
f) combining the reaction mixture from step e) with KY, wherein KY is KCl, KBr or KI;
g) maintaining the reaction mixture from step f) for at least 4 hours; and
h) recovering oxaliplatin from the reaction mixture obtained in step g).

3. The process of claim 2, wherein the basic solution of silver oxalate of step d) has a pH of about 4.5 to about 5.0.

4. The process of claim 2, wherein the reaction mixture in step e) is heated to a temperature of about 55° C. to about 60° C.

5. The process of claim 2, wherein the potassium salt of the form KY is KI.

6. The process of claim 2, wherein the oxaliplatin has less than about 3% area by HPLC of the cis-oxalato-(trans-D-1, 2-cyclohexanediamine) Pt (II) complex isomer.

7. The process of claim 2, further comprising purifying the oxaliplatin obtained in step h) by dissolving it in water, removing the remaining silver ions from the reaction mixture and crystallizing oxaliplatin.

8. The process of claim 7, further comprising, after crystallizing the oxaliplatin, crystallizing the oxaliplatin in a solvent selected from the group consisting of an amide, a $C_{1-4}$ alkyl ester, a ketone, a halogenated hydrocarbon, water and mixtures thereof.

9. The process of claim 8, wherein the organic solvent is dimethylformamide.

10. The process of claim 7, wherein the silver ions are removed by a method selected from:
precipitation of silver halide by addition of a potassium halogenated salt to the solution of oxaliplatin in water,
using a chelating agent, and
using a cation exchange resin.

11. A process for preparing oxaliplatin, comprising:
(i) conducting a process of preparing cis-diiodo-(trans-L-1,2-cyclohexanediamine) Pt (II) complex comprising:
   a) combining trans-L-1,2-cyclohexanediamine of the formula (5)

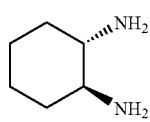

(5)

with $M_2PtX_4$ and KI to obtain a mixture;
   b) maintaining the mixture at room temperature; and
   c) recovering cis-diiodo-(trans-L-1,2-cyclohexanediamine) Pt (II) complex,
   wherein M is Li, Na or K, and
   wherein X is I, Cl or Br;
(ii) reacting the cis-diiodo-(trans-L-1,2-cyclohexanediamine) platinum (II) complex obtained in step c) with silver nitrate to obtain cis-diaquo-(trans-L-1,2-cyclohexanediamine) Pt (II) complex in a reaction mixture;
(iii) removing silver ions from the reaction mixture;
(iv) recovering the cis-diaquo-(trans-L-1,2-cyclohexanediamine) Pt (II) complex;
(v) converting the cis-diaquo-(trans-L-1,2-cyclohexanediamine) Pt (II) complex to oxaliplatin; and
(vi) recovering the oxaliplatin.

12. The process of claim 11,
wherein step (ii) is performed by
   d) combining the cis-diiodo-(trans-L-1,2-cyclohexanediamine) platinum (II) complex with an aqueous solution of silver nitrate to obtain a reaction mixture;
   e) heating the reaction mixture to a temperature of about 45° C. to about 60° C. to obtain a suspension of cis-diaquo-(trans-L-1,2-cyclohexanediamine) Pt (II) complex; and
   f) cooling the suspension to a temperature of about 20° C. to about 30° C.

13. The process of claim 12, wherein the reaction mixture in step e) is heated to a temperature of about 45° C. to about 55° C.

14. The process of claim 11, wherein the silver ions are removed from the reaction mixture by the precipitation of silver iodide obtained from the addition of KI.

15. The process of claim 11, wherein the cis-diaquo-(trans-L-1,2-cyclohaxanediamine) Pt (II) complex is converted into oxaliplatin by
   combining it with potassium oxalate;
   adjusting the pH to about 4.5 to about 5.0;
   cooling to obtain a suspension of cis-oxalato-(trans-L-1,2-cyclohexanediamine) Pt (II) complex; and recovering cis-oxalato-(trans-L-1,2-cyclohexanediamine) Pt (II) complex from the suspension.

16. The process of claim 11, wherein the oxaliplatin has less than about 3% area by HPLC of the cis-oxalato-(trans-D-1,2-cyclohexanediamine) Pt (II) complex isomer.

17. A process for preparing oxaliplatin comprising the steps of:
   a) combining an aqueous solution of trans-L1,2-cyclohexanediamine of formula (5)

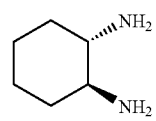

(5)

with an aqueous solution of $M_2PtX_4$ and KI to obtain a mixture;
   b) maintaining the mixture at room temperature;
   c) recovering cis-diiodo-(trans-L-1,2-cyclohexanediamine) Pt (II) complex; and
   d) converting the cis-diiodo-(trans-L-1,2-cyclohexanediamine) Pt (II) complex into oxaliplatin,
   wherein M is Li, Na or K, and
   wherein X is I, Cl or Br.

* * * * *